(12) United States Patent
Van Mooy et al.

(10) Patent No.: US 9,188,512 B2
(45) Date of Patent: Nov. 17, 2015

(54) AQUATIC SAMPLE ANALYSIS SYSTEM

(75) Inventors: Benjamin A. S. Van Mooy, Falmouth, MA (US); Richard G. Keil, Seattle, WA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 25 days.

(21) Appl. No.: 13/476,531

(22) Filed: May 21, 2012

(65) Prior Publication Data

US 2013/0068011 A1 Mar. 21, 2013

Related U.S. Application Data

(60) Provisional application No. 61/488,454, filed on May 20, 2011.

(51) Int. Cl.
| | | |
|---|---|---|
| G01C 5/00 | (2006.01) | |
| G01C 13/00 | (2006.01) | |
| G01D 1/00 | (2006.01) | |
| G01D 3/00 | (2006.01) | |
| G01D 11/24 | (2006.01) | |
| G01D 21/00 | (2006.01) | |
| G01F 1/00 | (2006.01) | |
| G01F 3/00 | (2006.01) | |
| G01F 11/00 | (2006.01) | |
| G01F 15/00 | (2006.01) | |
| G01F 23/00 | (2006.01) | |
| G01N 1/00 | (2006.01) | |
| G01N 1/10 | (2006.01) | |
| G01P 13/00 | (2006.01) | |

(Continued)

(52) U.S. Cl.
CPC .............. *G01N 1/10* (2013.01); *G01N 33/1826* (2013.01); *G01N 33/18* (2013.01); *G01N 33/1806* (2013.01); *G01N 33/1886* (2013.01)

(58) Field of Classification Search
CPC .. G01N 1/10; G01N 33/1806; G01N 33/1886
USPC .......... 73/170.29, 866.5, 53.01, 61.59, 61.68, 73/170.33
See application file for complete search history.

(56) References Cited

U.S. PATENT DOCUMENTS 3,241,811 A * 3/1966 Kilbourne ...................... 251/288
3,845,303 A * 10/1974 Richards et al. .............. 250/303

(Continued)

FOREIGN PATENT DOCUMENTS

DE 102008047905 A1 4/2010

OTHER PUBLICATIONS

Lefevre et. al., "WP3: Science Missions," Nov. 27, 2009, http://www.eurosites.info/pdf/IODA_WP3_report_nov_2009.pdf, (5 pages).*

(Continued)

*Primary Examiner* — Laura Martin
*Assistant Examiner* — Rhyan C Lange
(74) *Attorney, Agent, or Firm* — Goodwin Procter LLP (57) ABSTRACT

According to one aspect, the invention relates to an aquatic sample analysis system adapted for in situ use. The system includes an incubation chamber having an optically clear portion and forming an opening for receiving a fluidic sample and apparatus for sealing the opening. The system also includes a sensor for sensing at least one parameter associated with the sample inside the chamber, a control module in communication with the sensor, and a power source.

21 Claims, 5 Drawing Sheets

(51) Int. Cl.
*G08C 19/00* (2006.01)
*G01N 33/18* (2006.01)

(56) References Cited

U.S. PATENT DOCUMENTS

2006/0091319 A1* 5/2006 Steuerwald et al. .......... 250/373
2011/0214500 A1* 9/2011 Cabrera et al. ............. 73/170.29

OTHER PUBLICATIONS

Selvaraj, "Validity of net primary productivity estimation by light and dark bottle oxygen technique in tropical inshore waters, with a note on primary productivity of the surf zone at Cochin," 2000, http://eprints.cmfri.org.in/5934/1/Article_03.pdf, (8 pages).*
Bellerby et al., "Shipboard flow injection determination of sea water pH with spectrophotometric detection," Analytica Chimica Acta, vol. 309, No. 1-3, Jun. 1995, pp. 259-270.
Del Giorgio and Duarte, "Respiration in the open ocean," Nature, vol. 420, Nov. 28, 2002, pp. 379-384.
Dominique et al., "WP3: Science Missions," XP55034507A, Nov. 27, 2009, http://www.eurosites.info/pdf/IODA_WP3report_nov_2009.pdf,( 5 pages).
Drazen et al., "Development of a hyperbaric trap-respirometer for the capture and maintenance of live deep-sea organisms," Limnology and Oceanography: Methods, vol. 3, Nov. 2005, pp. 488-498.
Hoppe et al., "Bacterial growth and primary production along a north-south transect of the Atlantic Ocean," Nature, vol. 416, Mar. 14, 2002, pp. 168-171.

International Search Report and Written Opinion for PCT/US2012/038857 mailed Aug. 16, 2012, (12 pages).
Larkin, "EuroSITES Open Ocean Observatory Network: Monitoring Europe's Open Ocean," http://www.earthzine.org/2010/06/26/eurosites-open-ocean-observatory-network-monitoring-europe%E2%80%99s-open-ocean/, XP002681201, Jun. 26, 2010, (6 pages).
Rivkin and Legendre, "Biogenic Carbon Cycling in the Upper Ocean: Effects of Microbial Respiration," Science, vol. 291, Mar. 23, 2001 pp. 2398-2400.
Robinson and Williams, Chapter 9, "Respiration and its measurement in surface marine waters," in "respiration in aquatic ecosystems" (del Giorgio and Williams eds.), Oxford University Press, 2005, pp. 147-180.
"Smart Sensor Technology Saves Feed Costs," Aanderaa Data Instruments, Pamphlet, Jul. 2006, (1 page).
Tamburini et al., "Role of deep-sea bacteria in organic matter mineralization and adaptation to hydrostatic pressure conditions in the NW Mediterranean Sea," Aquat. Microb. Ecol., vol. 32, Jul. 14, 2003, pp. 209-218.
"Oxygen-based Respirometer," slide from a Sep. 2009 presentation, (1 page).
Van Mooy, "Assessing Rates of Bacterial Carbon Demand in the Twilight Zone: Results from Vertigo and Future Approaches." Abstract, Sep. 2009, (2 pages).
Williams et al., Chapter 1, "Respiration in aquatic ecosystems: history and background," in "respiration in aquatic ecosystems" (del Giorgio and Williams eds.), Oxford University Press, 2005, pp. 1-17.
Williams, "The balance of plankton respiration and photosynthesis in the open oceans," Nature, vol. 394, Jul. 2, 1998, pp. 55-57.

* cited by examiner

AQUATIC SAMPLE ANALYSIS SYSTEM

CROSS-REFERENCE TO RELATED APPLICATION

This application claims priority to and the benefit of U.S. Provisional Patent Application Ser. No. 61/488,454, filed on May 20, 2011, the disclosure of which is hereby incorporated herein by reference in its entirety.

FIELD OF THE INVENTION

The present invention relates generally to in situ systems for analyzing parameters of interest in aquatic environments and, more specifically, to systems having multiple incubation chambers for providing comparative environmental conditions.

BACKGROUND OF THE INVENTION

The rates of photosynthesis and respiration define the role of lakes and oceans in the global carbon cycle: if photosynthesis exceeds respiration then the water is a sink for $CO_2$, while if respiration exceeds photosynthesis then it is a source of $CO_2$. Due to the relative ease of incubation-based $^{14}C$ primary production methods, the rate of photosynthesis has been measured many hundreds of thousands of times. Oceanographers and limnologists achieved a global view of photosynthesis rates by the late 1960s and the global database of $^{14}C$ primary production data continues to grow. This information has provided the biological basis for potent satellite- and model-based analyses of ocean biogeochemistry. In contrast, the rate of respiration has only been measured about 2000 times and, thus, there is no global-level understanding of aquatic respiration rates; this is a profound gap in our knowledge. In the ocean, the paucity of respiration rate data has fueled an intense debate over whether the ocean is a net source or sink of $CO_2$ on a global scale. Furthermore, there is very little incubation-based respiration data to assess regional scale $CO_2$ balances, even within the coastal waters of the United States. Given the importance of understanding $CO_2$ balance from both scientific and geopolitical standpoints, the demand for respiration rate data will skyrocket in the next few years.

One of the primary reasons that the study of aquatic respiration has fallen so far behind the study of photosynthesis is that respiration rates are difficult to measure. Heterotrophic bacteria play an important role in attenuating the flux of particulate organic carbon (POC) flux through the twilight zone (i.e. shallow but dark waters); along with zooplankton, heterotrophic bacteria contribute to both particle disaggregation and attendant organic carbon respiration. The rates of heterotrophic bacterial processes in the twilight zone are substantially slower than in the euphotic zone, and accurately measuring these rates in the twilight zone presents numerous technical challenges. Many current technologies for measuring photosynthesis or respiration involve removing samples from their environment for incubation. A widely-applied tactic is to bring twilight zone water samples to the surface and apply scaled up versions of incubation-based methods originally designed for use in the euphotic zone; these methods are applied at atmospheric pressure and the effects of depressurization are assumed to be negligible. This has been done for measuring rates of tritiated thymidine incorporation by heterotrophic bacteria. The thymidine incorporation rates can be compared to rates of bacterial carbon demand (BCD) and, although this rate conversion imparts large uncertainties, comparisons can be made between BCD, zooplankton carbon demand, and the loss of sinking POC flux. These results showed, both in North Pacific subtropical gyre and the subarctic North Pacific, that twilight zone BCD greatly exceeded the loss of POC, suggesting either: 1) that BCD was overestimated; 2) that POC flux attenuation was underestimated; or 3) that there were additional, large sources of organic carbon to the twilight zone. Therefore, the rates of BCD should be better constrained. For example, enzymatic POC hydrolysis rates determined during testing can add some additional bounds to the BCD dataset. However, further bounds are still needed.

Another surface method is to incubate seawater (light and dark) and measure the decrease in oxygen concentrations using the Winkler titration method, as is known in the art. The Winkler titration can be messy, time consuming, and error prone and, as such, a major impediment to the study of respiration at sea. Alternative methods have been attempted, such as measuring oxygen with electrodes or tracking an increase of $CO_2$, but these have not shown the reliability and sensitivity of the Winkler titration. Unlike photosynthesis, respiration is not confined to the sunlit waters of the ocean's surface. This is because organic particles from photosynthetic organisms sink from the surface waters to the mesopelagic, where most of them are ultimately respired. Since the Winkler titration is a wet chemical method, oxygen measurements of mesopelagic waters must be conducted on the deck of ship. This again introduces biases caused by depressurization of the microbes responsible for respiration. Some studies that have addressed the impact of pressure on microbial respiration suggest that the depressurization biases may be quite large, even at relatively shallow depths (e.g., 100s of meters).

Radioisotope methods can provide simple yet sensitive measurements; however, these methods are not generally available for measuring respiration rates. One method is performed partially in situ. This approach requires that the device sample and filter the incubation, and that these filters be retrieved using a research vessel in order to quantify the desired process (e.g., to measure photosynthesis and respiration). However, this method (and other radioisostope systems) have the disadvantage of being subject to regulatory constraints associated with the use of radioactive substances in the ocean.

Photosynthesis and respiration are arguably the defining parameters of carbon cycling in aquatic ecosystems (freshwater and saltwater), and are also primary components of oxygen demand measurements (i.e., biological oxygen demand ("BOD")) in the water quality community. Almost every municipality makes BOD measurements as part of their wastewater management operations. The ability to easily make such measurements is also of interest in the oceanographic community and plays a key role in the Ocean Observatories Initiative.

Accordingly, there exists a need in the art for a reliable, cost-effective, in situ system for analyzing aquatic parameters of interest, such as determining respiration rates.

SUMMARY OF THE INVENTION

The present invention is directed toward novel systems and methods for analyzing aquatic parameters in situ, such as through the use of a Photosynthesis Respiration and Carbon Balance Yielding Sensor ("PHORCYS"). The PHORCYS may use an oxygen optode, for aquatic respirometry. The PHORCYS allows incubations under in situ conditions, which more faithfully mimics the "real world" conditions. This is a major advance over existing approaches, most of which are one-off lab-based systems and which suffer from changes in temperature, light and pressure associated with removal of water from the in situ conditions, as described above. The PHORCYS system does not require chemicals of any kind, nor does it produce a sample that must be collected. The system can produce data continuously, without the need for recovery aboard ship or additional sample processing.

According to one aspect, the invention relates to an aquatic sample analysis system adapted for in situ use. The system includes an incubation chamber having an optically clear portion and forming an opening for receiving a fluidic sample and a seal for sealing the opening. The system also includes a sensor for sensing at least one parameter associated with the sample inside the chamber, a control module in communication with the sensor, and a power source.

In accordance with one embodiment of the above aspect, the chamber includes a tube with at least one open end covered by the seal. At least one open end may be sealable with a spring-loaded cap, which may be biased toward a sealing position. In another embodiment, the at least one open end is sealable with a ball valve, and/or the at least one open end is sealable with a hinged cap. In some embodiments the parameter may be oxygen concentration, nitrate concentration, carbon dioxide concentration, or pH. The sensor may be an oxygen optode, a UV-based nitrate detector, a colorimetric carbon dioxide sensor, and/or a colorimetric pH sensor. The control module may be adapted to provide power to the sensor and receive sensor output, and may also store the sensor output and/or transmit the sensor output.

In other embodiments, the system includes an optically opaque incubation chamber. The opaque chamber may include a sensor for sensing at least one parameter associated with a sample inside the opaque chamber. The parameter may be oxygen concentration, nitrate concentration, carbon dioxide concentration, or pH. The control module may be adapted to compare respective outputs of the clear chamber sensor and the opaque chamber sensor, and may be adapted to determine instantaneous oxygen concentration, gross respiration rate, gross primary production rate, and/or net primary production rate.

In another aspect, the invention relates to a method of analyzing an aquatic parameter in situ. The method includes the steps of deploying an aquatic sample analysis system to a location and depth of interest and obtaining a fluidic sample at the location and depth of interest. The method also includes measuring a parameter of interest associated with the sample over an incubation period, determining a rate-of-change of the parameter of interest, and calculating at least one of a gross respiration rate, a gross primary production rate and a net primary production rate based at least in part thereon.

In accordance with one embodiment of the foregoing aspect, the aquatic sample analysis system includes an incubation chamber including an optically clear portion and an optically opaque incubation chamber. The fluidic sample may be disposed in each incubation chamber. In some embodiments, the parameter of interest is oxygen concentration. The method may also include releasing a fluidic sample and obtaining a new fluidic sample, and may further include transmitting data based at least in part on the parameter of interest from the system to a remote location.

In still other embodiments, the calculating step includes calculating gross respiration rate based at least in part on rate-of-change of oxygen concentration in the optically opaque incubation chamber, calculating net primary production rate based at least in part on rate-of-change of oxygen concentration in the optically clear incubation chamber, and determining gross primary production rate based thereon. The incubation period may occur at least partially during daylight.

BRIEF DESCRIPTION OF THE FIGURES

Other features and advantages of the present invention, as well as the invention itself, can be more fully understood from the following description of the various embodiments, when read together with the accompanying drawings, in which.

DETAILED DESCRIPTION OF THE INVENTION

The invention may be better understood by reference to the following detailed description, taken in conjunction with the figures. Various embodiments of the invention relate to a system for analyzing aquatic parameters in both freshwater and saltwater. Other configurations and variants will be apparent to those skilled in the art from the teachings herein and are considered to be within the scope of the invention.

The PHORCYS system is in various embodiments an expandable and versatile family of instruments containing one or more incubation chambers and a unique combination of sample collection systems and sensors that are used to measure photosynthesis and respiration in aquatic and marine systems under in situ conditions. The PHORCYS system may be deployed directly into aquatic and marine environments, operate underwater, and incubate fluidic samples in situ. The system, in various embodiments, makes use of the classical approach of tracking dissolved species involved in photosynthesis and respiration (i.e., oxygen, nitrate, carbon dioxide, pH, etc.) over an incubation period. Various embodiments may share four basic elements: 1) an optically clear and/or opaque incubation container/chamber that collects water; 2) a system to open and close the incubation container(s), thereby initiating and terminating the incubation period(s); 3) oxygen, nitrate, carbon dioxide or pH sensors, and/or variants thereof (including for concentration); and 4) an electronics unit/control module, which may provide power, record data, and/or transmit data. Still other embodiments of the PHORCYS instruments include apparatus to add substances such as solutions and/or particles to determine their impact on respiration or primary production. Other embodiments include devices to take water samples during the course of incubation, and automated valves for opening, rinsing and closing the incubation chambers. Some embodiments may depend on external rigging to position the PHORCYS instrument in the appropriate location of the water column and proper orientation to collect and incubate samples under in situ conditions, such as a drifting array, anchored mooring, or lowering it from a pier or ship into the water. Other embodiments may be self-ballasting and self-orienting, and may be part of a networked ocean observatory system or incorporated into autonomous underwater vehicles and permanently reside in the ocean. Communications systems to transmit data to and/or receive data from a remote location are also contemplated and considered within the scope of the invention.

Figure 1:
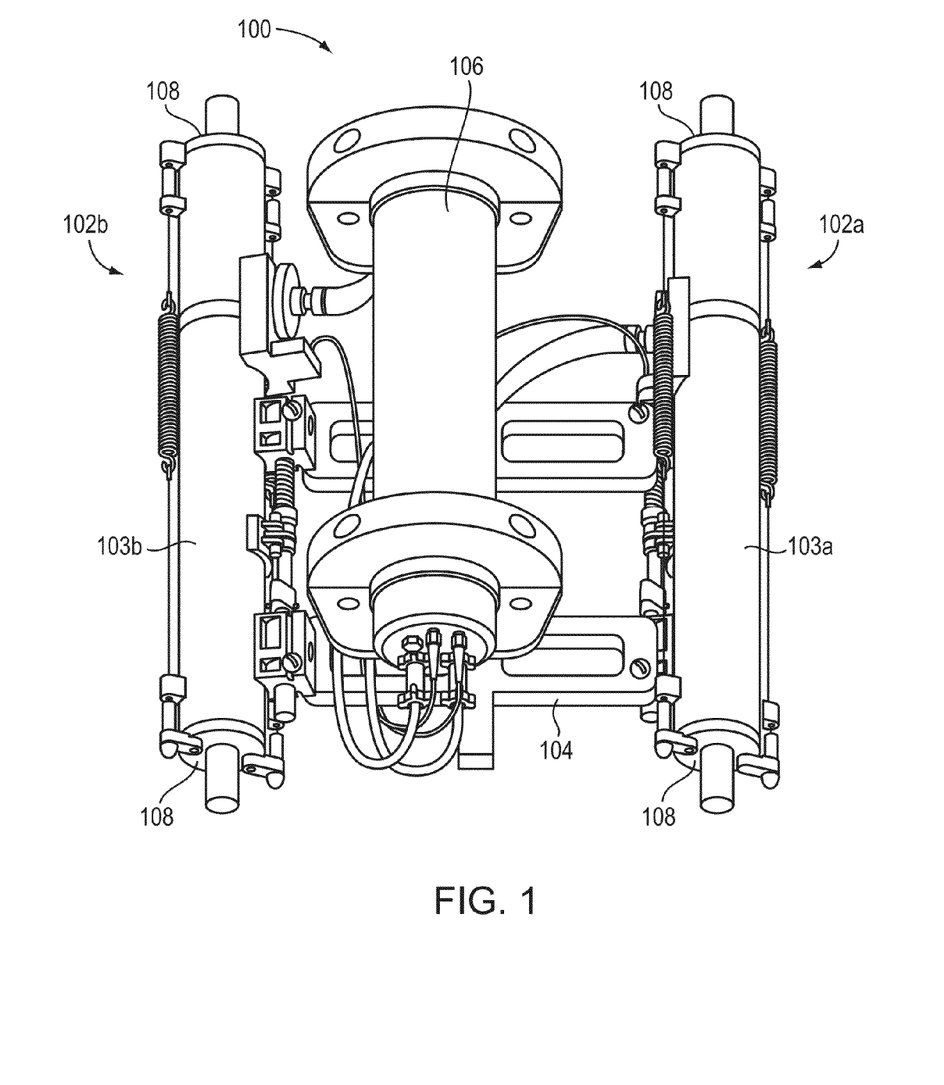
FIG. 1 is a schematic, front perspective view of an aquatic sample collection system, in accordance with one embodiment of the invention.

One embodiment of an aquatic sample analysis system 100 may be seen in FIG. 1. The system 100 includes an incubation chamber 102a with a substantially optically clear (i.e., transparent, translucent; allows for passage of ambient light) portion 103a (the clear chamber) and an incubation chamber 102b with a substantially optically opaque (i.e., blocks ambient light) portion 103b (the dark chamber), each of which contains a sensor, such as an oxygen optode (as described in greater detail below). The incubation chambers 102a, 102b may be generally cylindrical and are mounted to a common frame 104 with a control module housing 106 that houses a control module in communication with one or more sensors. The control module 106 also operates spring-loaded caps 108 between an open position to allow water to enter the incubation chambers 102a, 102b (and similarly to allow any water already present to leave) and a closed position to enclose water (e.g., obtain a fluidic sample) in the incubation chambers 102a, 102b to initiate incubation. In certain embodiments, the chambers 102a, 102b may be sealed with hinged caps or some other closure mechanism or seal (e.g., ball valves). FIG. 1 depicts the chambers 102a, 102b having openings at both ends, though it is possible there is only one opening to the chamber 102a, 102b (and the opening does not necessarily have to be at one end thereof). The system 100 also includes a power source disposed in the control module housing 106. The components of the system 100 allow a water (freshwater or saltwater) sample to be enclosed, incubated in situ, and monitored for changes in oxygen concentration at a depth of interest. In some embodiments, only a single incubation chamber (e.g., incubation chamber 102a) may be used. In variations having only one open end, only one closure may be necessary to seal a chamber opening.

Figure 2:
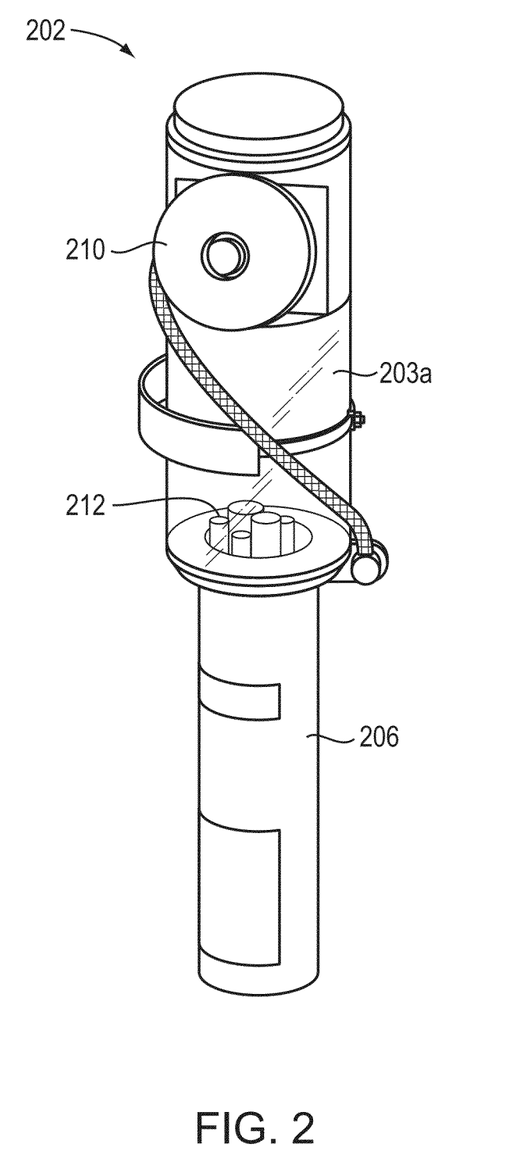
FIG. 2 is a schematic, front perspective view of an incubation chamber usable with the aquatic sample collection system of FIG. 1, in accordance with another embodiment of the invention.

Another embodiment of an incubation chamber 202 for use with the system 100 (either in addition to, or instead of, at least one of the incubation chambers 102a, 102b) is depicted in FIG. 2. The incubation chamber 202 has at least one ball valve 210 (there may be more than one, such as dual ball valves) to seal the incubation chamber 202. The ball valve 210 may be only on one side of a semi-transparent portion 203a of the incubation chamber 202, thereby allowing water in and out on one side of the semi-transparent portion 203a. Sensors 212, such as those described above, including an oxygen optode, may be located opposite the ball valve 210 on the opposite end of the semi-transparent portion 203a. A separate control module housing 206 containing a control module to control the ball valve 210 and/or the sensors 212 is also located opposite the ball valve 210. In certain embodiments, the ball valve(s) 210 may be configured to repeatedly open and close the incubation chamber 202. Two or more semi-transparent portions 203a may be used, particularly when the chamber 202 is intended to be deployed in dark ambient settings where replicate respiration measurements are made. The chamber 202 can be attached to other devices, such as sediment traps, in order to enhance particle concentrations within the chambers.

Figure 3A:
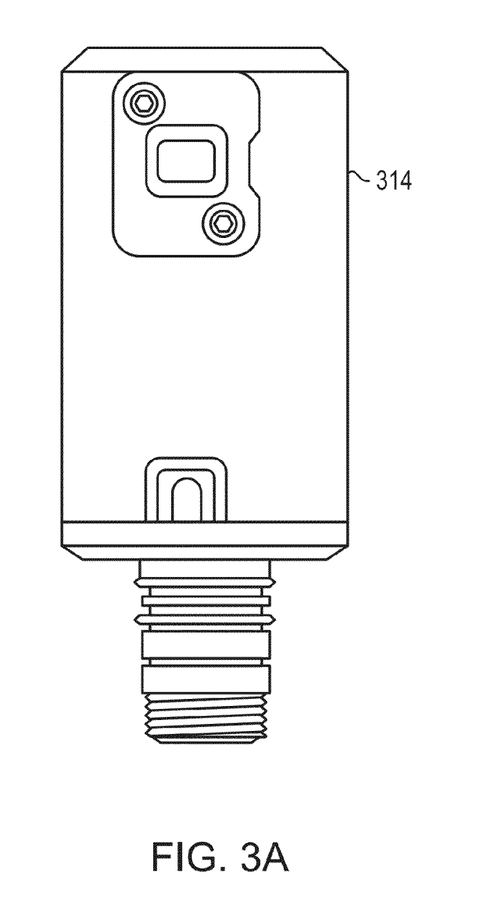
FIG. 3A is a schematic front view of an oxygen optode for use with an incubation chamber, in accordance with one embodiment of the invention.
Figure 3B:
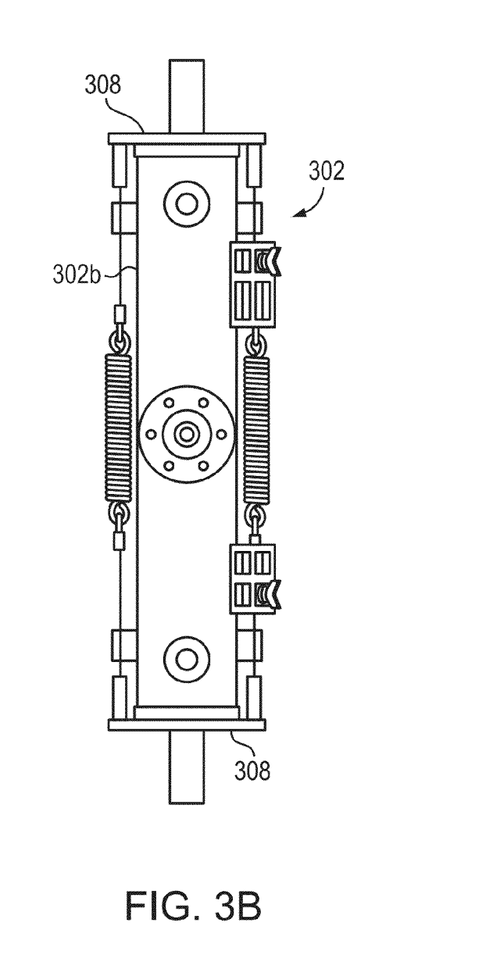
FIG. 3B is a schematic front view of an incubation chamber usable with the oxygen optode of FIG. 3A, in accordance with one embodiment of the invention.

FIG. 3A depicts an oxygen optode 314 for use with an aquatic sample analysis system, and may be particularly adapted to be disposed in a chamber as described above (also in a chamber 302 with opaque walls as depicted in FIG. 3B). The oxygen optode 314 may contain optical sensors that utilize a fluorescent platinum porphyrin complex embedded in a gas permeable foil that is exposed to the surrounding water. The fluorescence phase of the foil is proportional to the concentration of oxygen in the surrounding water. This sensing foil is attached to a window in a watertight titanium housing that contains the optical instruments. Through the window, the foil is excited by modulated blue light and the phase of a returned red fluorescent light is measured using a photodiode. These sensors are designed to work under in situ pressures and temperatures. Unlike $O_2$ electrodes, optodes do not consume oxygen and are thus advantageous for measuring changes in oxygen concentration in confined vessels, such as the incubators.

Some oxygen optodes, such as the Aanderaa oxygen optode (Aanderaa Data Instruments, Inc., Attleboro, Mass.) can measure oxygen with high resolution and accuracy and allow the PHORCYS system to measure respiration rates as low as about 1 $\mu$mol $O_2$ $L^{-1}$ $d^{-1}$. In it present embodiments, the sensitivity of the PHORCYS system is limited only by the stability, accuracy and precision of the sensors, such as the oxygen optode, that are contained with in it. This sensitivity, which is similar to and may exceed the resolution of the Winkler titration method (comparative results using both methods are shown in Table 1), supports effective determination of respiration rates in most aquatic waters with oxygen optodes. Moreover, whereas the Winkler method relies on solely a few measurements to establish rate-of-change of $O_2$ concentration, thousands of respiration rate measurements may be made with optode-based respirometers, providing greatly improved confidence in measured data results. Such systems, according to the invention, may be deployed effectively in various applications, such as on wired ocean observing networks or autonomous profilers/gliders.

TABLE 1

| | |
|---|---|
| Standard BOD with Winkler: | 5.04 ± 0.12 $\mu$mol $O_2$ $L^{-1}$ $d^{-1}$ |
| PHORCYS: | 2.770 ± 0.249 $\mu$mol $O_2$ $L^{-1}$ $d^{-1}$ |
| Standard BOD with Winkler: | 7.89 ± 0.34 $\mu$mol $O_2$ $L^{-1}$ $d^{-1}$ |
| PHORCYS: | 8.100 ± 0.340 $\mu$mol $O_2$ $L^{-1}$ $d^{-1}$ |
| Standard BOD with Winkler: | 31.2 ± 2.3 $\mu$mol $O_2$ $L^{-1}$ $d^{-1}$ |
| PHORCYS: | 31.66 ± 0.49 $\mu$mol $O_2$ $L^{-1}$ $d^{-1}$ |

Figure 4:
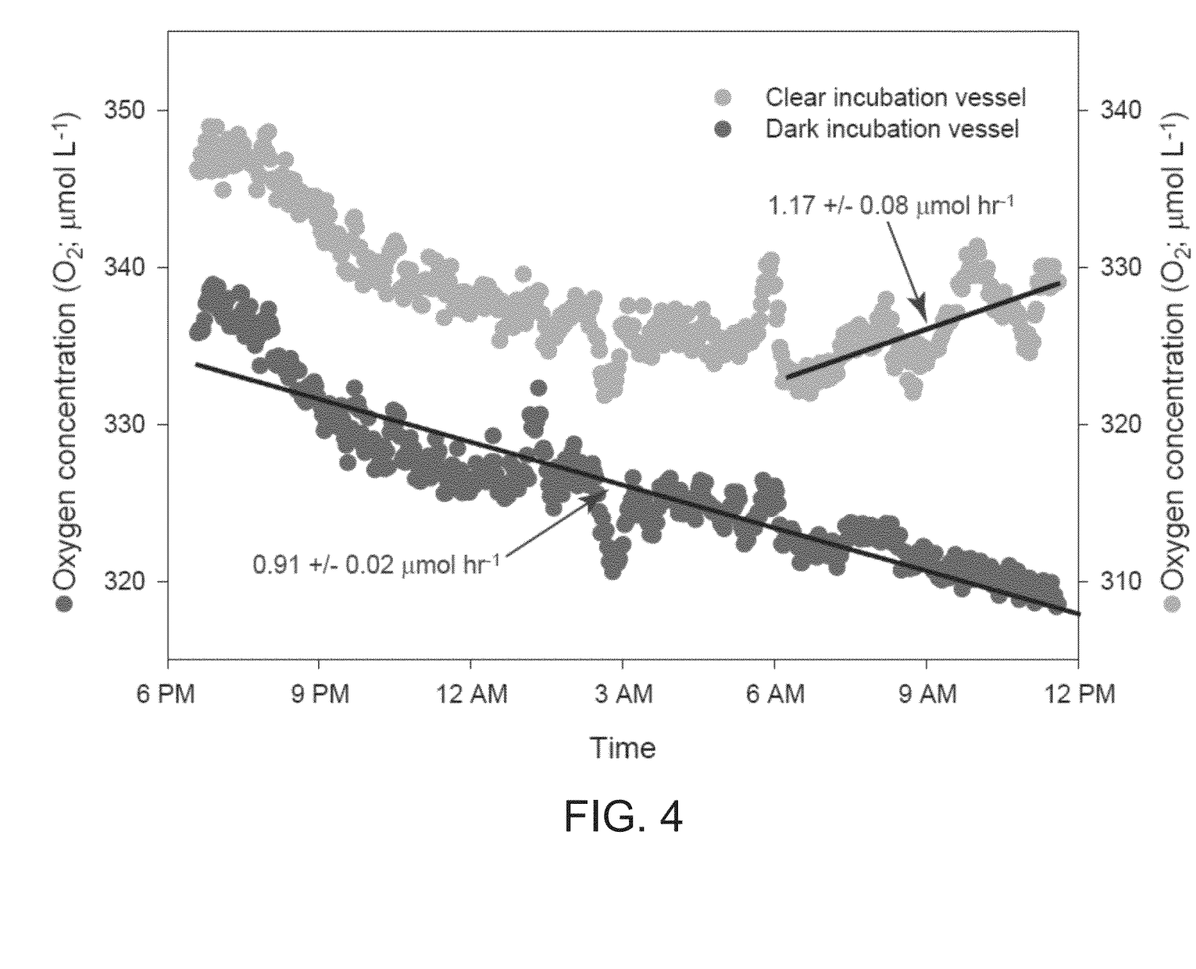
FIG. 4 is a graph of oxygen concentrations over time based on data collected with the aquatic sample collection system of FIG. 1.

The system 100 instruments collect data over time, such as oxygen concentrations as detected by an optode-type oxygen sensor, as depicted in FIG. 4, though other data may be collected depending on the sensors used, including nitrate concentration, carbon dioxide concentration, and pH. The dark/opaque incubation chamber 102b records the decrease in oxygen due to respiration. Respiration is also observed in the clear incubation chamber 102a during the night. Upon sunrise (approximately 6 AM in the graph in FIG. 4) oxygen concentrations in the clear chamber 102a reflect the sum of gross respiration and gross primary production; this sum is also known as net primary production. In the above example, the gross respiration rate is 0.91±0.02 $\mu$mol $O_2$ $hr^{-1}$ and the net primary production rate is 1.17±0.08 $\mu$mol $O_2$ $hr^{-1}$. Thus, the gross primary production rate is 2.08±0.08 $\mu$mol $O_2$ $hr^{-1}$, as determined by the difference between the gross respiration rate (negative slope) and the net primary production rate (positive slope).

Figure 5:
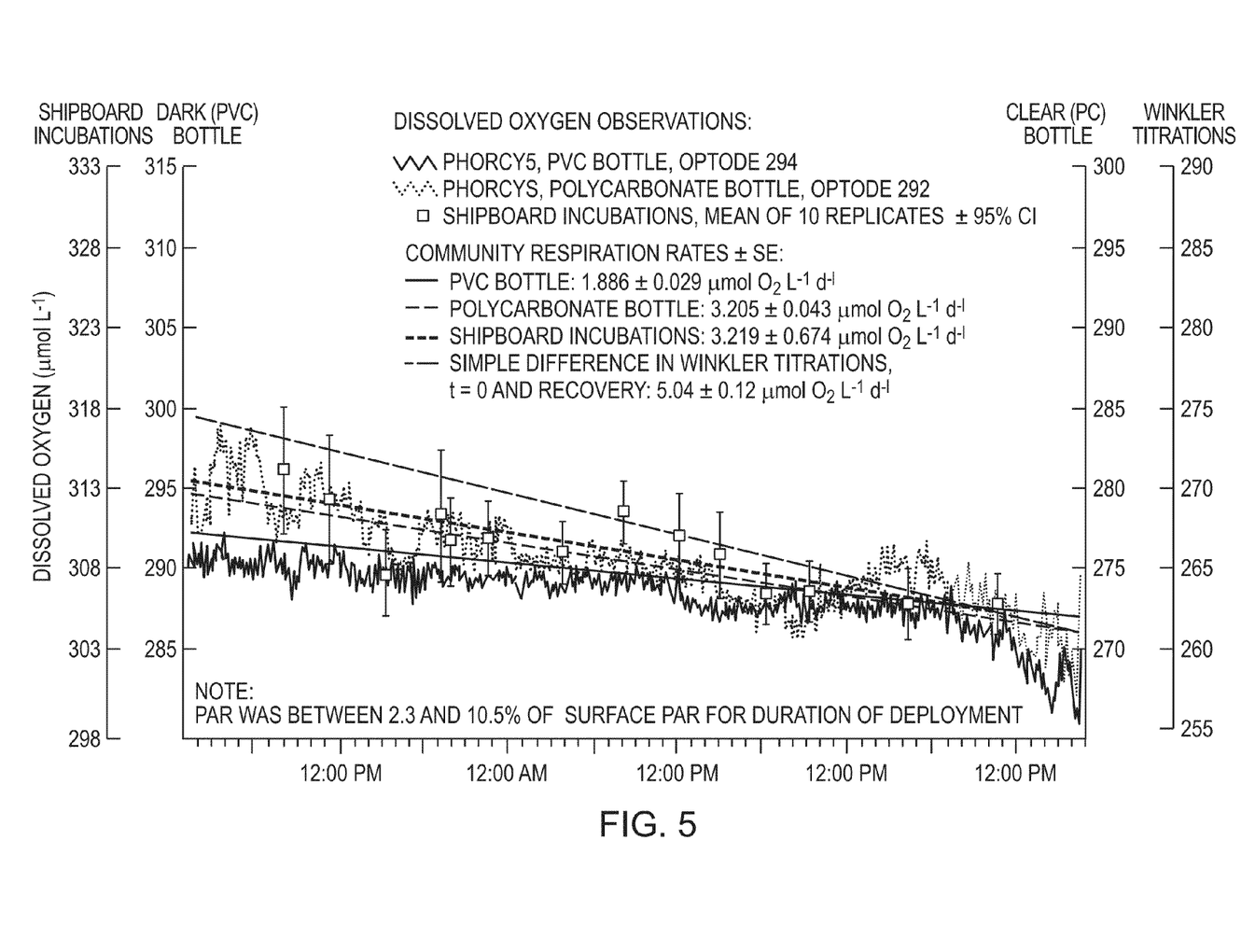
FIG. 5 is a graph of oxygen concentrations over time measured with different incubation chambers using an onboard method.

FIG. 5 depicts oxygen concentration results from additional testing, plotting results from the clear chamber 102a, the dark chamber 102b, and from shipboard incubations on the same graph. These results were obtained when the system 100 was disposed at a depth of approximately 29 m, at depth in the ocean that was effectively dark. The clear chamber 102a and the dark chamber 102b provide continuous results throughout the testing, allowing a user to follow variations in results to identify specific times of interest, in contrast to the periodic observations from shipboard incubations. Since the clear chamber 102a and the opaque chamber 102b remained in situ throughout the incubation, these results will be recognized by those skilled in the art as being more authentic representations of natural respiration rates than the shipboard incubations. Further, as evidenced by the much smaller errors in respiration rates, the continuous measurements in the clear chamber 102a and the dark chamber 102b demonstrate greater sensitivity to changes in the fluidic sample than the results from the onboard incubations; this is particularly true of respiration rates based on the Winkler method, which is mostly widely practiced by those skilled in the art.

The operational ranges of the system are generally dictated by the sensors. Presently, oxygen sensors, such as those from Aanderaa mentioned above, are rated to 6,000 m depth (approximately 95% of all of the ocean is shallower than 6,000 m). The temperature range of this sensor is −5 to +40° C. However, the use of other sensors with greater pressure handling capabilities and different temperature ranges are contemplated, and considered within the scope of the invention. Also, the incubation chambers may typically each have a volume between about 1 and about 10 liters, though the chambers may be as small as about 1 mL or less or as large as about 50 L (or more), depending on the application. In principle, the chambers may be configured to be any shape or volume, and may be made of any functionally biologically inert material, such as quartz or polytetrafluoroethylene.

In some embodiments, the system 100 is programmed before being deployed, e.g., by programming the control module. The programmable parameters may include the times at which the chambers 102a, 102b close and open to control the incubation period, the frequency of data collection by the sensors, power management, and mechanisms for data storage and/or transmission. These parameters may also be controlled in real time through wired or wireless communications with the control module. In other embodiments, the system's incubation chambers 102a, 102b close automatically, and then remain closed until the incubation period is over. For example, the spring-loaded lids 108 depicted in FIG. 1 may snap shut on the chambers 102a, 102b after they are triggered by a burn wire once the system reaches a desired depth. Some embodiments of the system 100 can conduct multiple incubations by closing and opening the chambers 102a, 102b repeatedly, and acquire, process, and transmit data from multiple incubations. Some embodiments include injection systems to introduce other materials, such as particulate matter or dissolved chemicals, into the incubation chambers 102a, 102b, so that the impact of these other materials on respiration or primary production can be assessed.

Various embodiments and features of the present invention have been described in detail with particularity. The utilities thereof can be appreciated by those skilled in the art. It should be emphasized that the above-described embodiments of the present invention merely describe certain examples implementing the invention, including the best mode, in order to set forth a clear understanding of the principles of the invention. Numerous changes, variations, and modifications can be made to the embodiments described herein and the underlying concepts, without departing from the spirit and scope of the principles of the invention. All such variations and modifications are intended to be included within the scope of the present invention, as set forth herein. The scope of the present invention is to be defined by the claims, rather than limited by the forgoing description of various embodiments. Accordingly, what is desired to be secured by Letters Patent is the invention as defined and differentiated in the claims, and all equivalents.

What is claimed is:

1. An aquatic sample analysis system adapted for in situ use, the system comprising:
   an optically opaque incubation chamber forming an opening for receiving a fluidic sample;
   a seal for sealing the opening;
   an oxygen sensor capable of sensing an oxygen concentration associated with the sample inside the chamber in real time;
   a control module in communication with the sensor and adapted to determine a gross respiration rate in daylight without influence of a production rate contribution and to repeatedly open and close the incubation chamber while in situ; and
   a power source.

2. The system of claim 1, wherein the chamber comprises a tube with at least one open end covered by the seal.

3. The system of claim 2, wherein the at least one open end is sealable by a seal consisting of a spring-loaded cap.

4. The system of claim 3, wherein the spring-loaded cap is biased toward a sealing position.

5. The system of claim 2, wherein the at least one open end is sealable with a valve, wherein the valve is capable of automatically and repeatedly opening and closing the incubation chamber when disposed.

6. The system of claim 2, wherein the at least one open end is sealable with a hinged cap.

7. The system of claim 1 further comprising an additional sensor for sensing at least one parameter associated with the fluidic sample, wherein the at least one parameter is selected from the group consisting of a nitrate concentration, a carbon dioxide concentration, and a pH.

8. The system of claim 1, wherein the system comprises at least one sensor selected from the group consisting of a UV-based nitrate detector, a colorimetric carbon dioxide sensor, and a colorimetric pH sensor.

9. The system of claim 1, wherein the control module is adapted to provide power to the sensor and receive a sensor output.

10. The system of claim 9, wherein the control module further stores the sensor output.

11. The system of claim 1 further comprising an optically clear incubation chamber.

12. The system of claim 11, wherein the clear chamber comprises a sensor for sensing at least one parameter associated with a sample inside the clear chamber.

13. The system of claim 12, wherein the at least one parameter is selected from the group consisting of an oxygen concentration, a nitrate concentration, a carbon dioxide concentration, and a pH.

14. The system of claim 12, wherein the control module is adapted to compare respective outputs of the clear chamber sensor and the opaque chamber sensor.

15. The system of claim 14, wherein the control module is adapted to determine at least one of an instantaneous oxygen concentration, a gross respiration rate, a gross primary production rate, and a net primary production rate.

16. A method of analyzing an aquatic parameter in situ comprising the steps of:
   deploying an aquatic sample analysis system to a location of interest;
   obtaining a fluidic sample within an optically opaque incubation chamber at the location of interest;

measuring during daylight an oxygen concentration associated with the sample over an incubation period in situ;

calculating a gross respiration rate without influence of a production rate contribution; and opening and closing repeatedly the incubation chamber while in situ to obtain additional fluidic samples.

17. The method of claim 16, wherein the aquatic sample analysis system further comprises an incubation chamber comprising an optically clear portion.

18. The method of claim 17, wherein a portion of the fluidic sample is disposed in each incubation chamber.

19. The method of claim 16, wherein the calculating step comprises:

calculating the gross respiration rate based at least in part on a rate-of-change of oxygen concentration in the optically opaque incubation chamber;

calculating a net primary production rate based at least in part on a rate-of-change of oxygen concentration in the optically clear incubation chamber; and determining a gross primary production rate based thereon.

20. The method of claim 16, further capably comprising:

releasing the fluidic sample repeatedly; and obtaining a new fluidic sample repeatedly.

21. The method of claim 16, further comprising the step of adjusting incubation conditions, wherein the incubation conditions comprise at least one of sensor parameters and incubation times.

\* \* \* \* \*

UNITED STATES PATENT AND TRADEMARK OFFICE
CERTIFICATE OF CORRECTION

PATENT NO.          : 9,188,512 B2
APPLICATION NO.     : 13/476531
DATED               : November 17, 2015
INVENTOR(S)         : Benjamin Van Mooy and Richard Keil It is certified that error appears in the above-identified patent and that said Letters Patent is hereby corrected as shown below:

Specification

In Column 1, before "Field of the Invention" the following should be inserted:

--STATEMENT OF RIGHTS TO INVENTIONS MADE UNDER FEDERALLY SPONSORED RESEARCH
This invention was made with Government support under OCE1155438 awarded by the National Science Foundation. The Government has certain rights in this invention.--

Signed and Sealed this
Tenth Day of May, 2016

Michelle K. Lee
*Director of the United States Patent and Trademark Office*